United States Patent
Thomke et al.

(10) Patent No.: US 7,241,074 B2
(45) Date of Patent: Jul. 10, 2007

(54) CLAMPING AND ARTICULATION ELEMENT

(75) Inventors: Roland Thomke, Bellach (CH); Vinzenz Burgherr, Bern (CH); Christian Lutz, Solothurn (CH); Damian Fankhauser, Bern (CH); Clemens Dransfeld, Niederlenz (CH); René Fischer, Zurich (CH)

(73) Assignee: Stryker Trauma S.A. (CH)

( * ) Notice: Subject to any disclaimer, the term of this patent is extended or adjusted under 35 U.S.C. 154(b) by 0 days.

(21) Appl. No.: 11/202,690

(22) Filed: Aug. 12, 2005

(65) Prior Publication Data

US 2006/0039750 A1 Feb. 23, 2006

(30) Foreign Application Priority Data

Aug. 20, 2004 (EP) .................................. 04405521

(51) Int. Cl.
*B25G 3/36* (2006.01)
*E04G 7/00* (2006.01)
*E04G 7/14* (2006.01)

(52) U.S. Cl. ........................... 403/385; 606/57; 24/545

(58) Field of Classification Search ................ 403/385, 403/384, 395, 289; 606/54–61, 63, 72–73; 24/514, 545, 569, 525

See application file for complete search history.

(56) References Cited

U.S. PATENT DOCUMENTS

| 4,483,334 | A |   | 11/1984 | Murray |        |
|-----------|---|---|---------|--------|--------|
| 4,620,533 | A | * | 11/1986 | Mears .......................... | 606/54 |
| 4,648,388 | A | * | 3/1987  | Steffee ......................... | 606/61 |
| 5,285,556 | A | * | 2/1994  | Shorin et al. ................. | 24/487 |
| 5,752,954 | A |   | 5/1998  | Mata et al. |        |
| 5,938,663 | A | * | 8/1999  | Petreto ......................... | 606/61 |
| 5,947,965 | A | * | 9/1999  | Bryan ........................... | 606/61 |
| 6,022,348 | A |   | 2/2000  | Spitzer |        |
| 6,080,153 | A | * | 6/2000  | Mata et al. .................... | 606/54 |
| 6,277,069 | B1|   | 8/2001  | Gray |        |

(Continued)

FOREIGN PATENT DOCUMENTS

DE 19854347 6/1999

(Continued)

OTHER PUBLICATIONS

Search Report from EP 1 627 608 A1 dated Jan. 27, 2005.

*Primary Examiner*—Daniel P. Stodola
*Assistant Examiner*—Nahid Amiri
(74) *Attorney, Agent, or Firm*—Lerner, David, Littenberg, Krumholz & Mentlik, LLP

(57) ABSTRACT

A one-piece clamping element has two opposing clamping jaws forming a laterally open cavity to receive a rod-shaped element. A hinge is located between the jaws, arranged opposite the cavity, and connecting the clamping jaws with one another and thus allowing them to be movable with respect to one another. Each clamping jaw has one bore, aligned flush with one another. One clamping jaw has a receptacle for an anti-rotation device. The receptacle makes it preferable—with the exception of an immediate tightening of the screw in this or another place of an external fixator clamping element used for the same patient—to use the clamping element only once and discarding it after use. Two identical clamping elements, with the possible exception of the size of the rod receptacle, can be placed on top of one another to form an articulation element.

20 Claims, 13 Drawing Sheets

U.S. PATENT DOCUMENTS

| | | |
|---|---|---|
| 6,342,054 B1 | 1/2002 | Mata |
| 6,616,664 B2 | 9/2003 | Bailey et al. |
| 6,702,814 B2 * | 3/2004 | Walulik et al. ............... 606/57 |
| 6,749,361 B2 * | 6/2004 | Hermann et al. ........... 403/399 |
| 6,842,949 B2 * | 1/2005 | Warren ..................... 24/135 N |
| 6,872,209 B2 * | 3/2005 | Morrison ..................... 606/61 |
| 6,916,319 B2 * | 7/2005 | Munting ..................... 606/61 |
| 2002/0077629 A1 | 6/2002 | Hoffman et al. |

FOREIGN PATENT DOCUMENTS

EP      1 184 000      3/2002

* cited by examiner

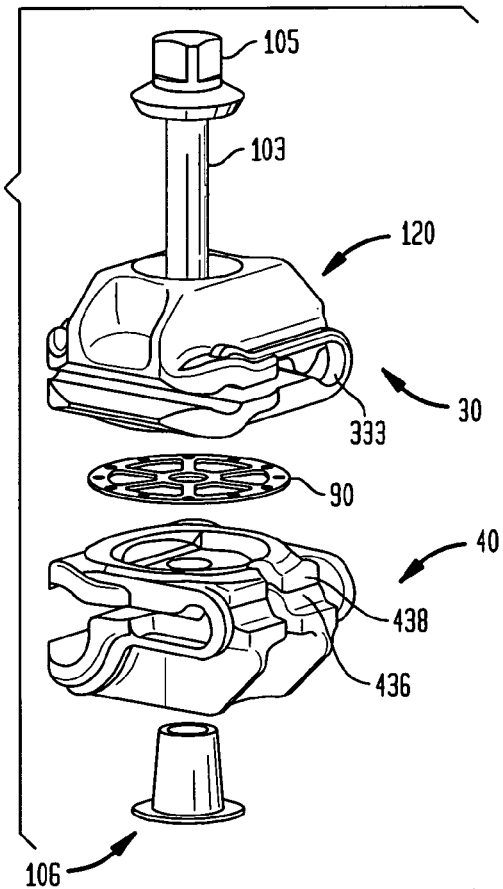
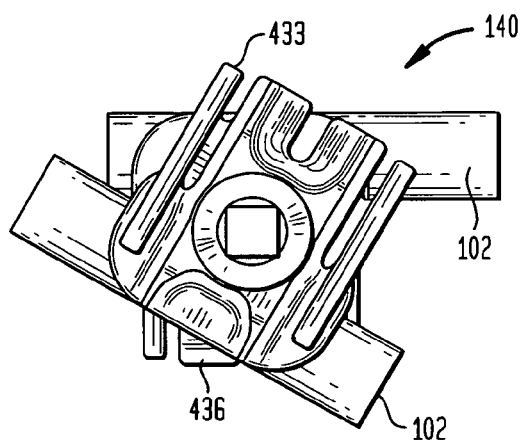
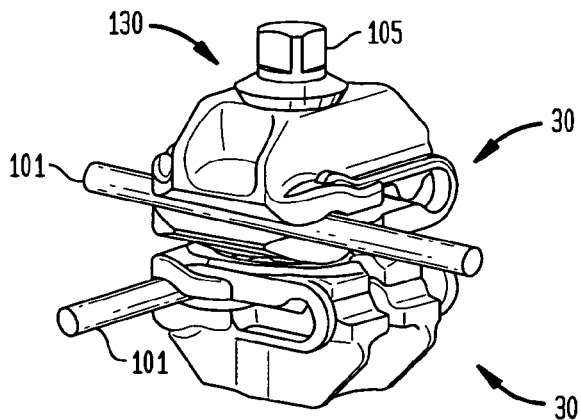

CLAMPING AND ARTICULATION ELEMENT

BACKGROUND OF THE INVENTION

The invention pertains to a clamping element for the clamping of a rod-shaped element of an articulation, element particularly a clamping element of an articulation element for the stabilization of bone fractures. The invention also pertains to an articulation element with two clamping elements and with one at least two-piece locking device.

EP 1 184 000 describes a single-piece clamping element with two opposing cavities and one laterally open cavity to receive a clamping jaw forming a rod-shaped element and a hinge, which is arranged opposite the cavity, connecting the clamping jaws so that they are movable on top of each other, with each clamping jaw having one bore each aligned flush with one another.

This clamping element has the advantage that an articulation can be produced with two identical clamping elements arranged next to one another, inserting a connecting screw through the bore, which is screwed into an internally threaded nut to close the clamping jaws.

One disadvantage of the known device is that the rod-shaped elements can be inserted into the receiving cavities only lengthwise from their ends.

From U.S. Pat. No. 6,277,069 another clamping element is known with a lateral opening. This permits the lateral insertion of a first rod-shaped element. A second rod-shaped element can be inserted in a closed sleeve connected with the clamping lever.

From U.S. Pat. No. 6,616,664 and U.S. Pat. No. 5,752,954 an articulation is known consisting of four individual clamping jaw elements and one central screw. This articulation allows the lateral insertion of one or two rod-shaped elements into the corresponding cavities. U.S. Pat. No. 5,752,954 has a spring arranged between the two center clamping jaw elements, which spring tension allows the clipping in of the rod-shaped elements and holding the jaw elements on the rod-shaped elements before the articulation element is blocked. U.S. Pat. No. 6,616,664 provides for narrow lateral lever arms to hold laterally inserted rod-shaped elements before the articulation is blocked. U.S. Pat. No. 6,342,054 has an external spring.

Based on this state of technology, it is one role of the invention at hand to indicate a simple single-piece clamping element which allows the lateral insertion of a rod-shaped element and which, when utilized dually, is directly applicable as an articulation element.

Another goal of the invention is the creation of a cost-effective disposable clamping element, particularly made of a synthetic material (such as plastic) injection molding, which does not have the structural disadvantages of X-ray transparent clamping elements as in EP 1 184 000.

Based on the known state of technology, another role of the invention is also to provide an improved articulation element.

SUMMARY OF THE INVENTION

A one-piece clamping element is provided comprising two opposing first and second clamping jaws forming a laterally open cavity to receive a rod-shaped element. At least one hinge element is arranged opposite the cavity connecting the two opposing clamping jaws to one another and thereby making them movable towards and away from one another. Each clamping jaw has a bore, aligned with one another. The hinge is resilient and the bores are arranged between the cavity and hinge. A first clamping jaw has an anti-rotation device on its exterior or a receptacle for receiving an anti-rotation device. The hinges include a resilient hinge wall, which merges into two parallel ribs formed in the first and second clamping jaws, which ribs run past the bore and which end in the area of a free end of at least one of the clamping jaws or which merge into the body of the one clamping jaw. The hinges include two resilient lateral bars, which each merge into the first and second clamping jaws. The lateral bars include a semi-circular centerpiece, followed by a transition bar at the transition into the first clamping jaw and followed by a longer bar at the transition into the second clamping jaw. The longer bar in the area of a wall adjacent to the cavity is connected with the second clamping jaw as a rib. The lateral bars are separated laterally from the clamping jaws by a slit. The hinges have a resilient and primarily C-shaped bar on the side of the clamping element opposite the cavity, each of which merges into the first and second clamping jaws. The hinges also have complementary stops which allow a pre-determined deflection about an axis of the resilient lateral bars before the stops come into contact. The bore in the first clamping jaw is cylindrical and has three or more longitudinal alignment ribs. The bore in the second clamping jaw conically narrows in the direction of the first clamping jaw and has an enlarged diameter step to receive the head of a screw or a nut. The bore has a lateral recess to receive an anti-rotation device of the nut.

An articulation element can be formed from two clamping elements in which the clamping elements are arranged on top of one another with their first clamping jaws adjacent one another. The articulation element has one at least two-piece locking shaft with a first part of the locking shaft insertable through a bore of the second clamping jaw of one clamping element, and with a second part of the locking shaft insertable through a bore of the first clamping jaw of the other clamping element. One or the other or both parts of the locking shaft being able to be brought in contact with one another through the bores in the first clamping jaws. The first and second clamping jaws of the clamping elements can be blocked with the locking device. The articulation element has an anti-rotation device is arranged between the first clamping jaws that are arranged on top of one another, the anti-rotation device having a central bore. The anti-rotation device is preferably a plate whose material is preferably harder than the material of the clamping elements and which has ridges formed on both sides of the plate. The anti-rotation device can also be a cylinder whose material in a floor and a lid area thereof is preferably harder than the material of the clamping elements, and which preferably consists of a flexible, compressible material in the solid material part, in particular synthetic foam. The locking device includes a cylindrical screw and a conical nut, the conical nut preferably has a stop shoulder for a self-locking screw, which can be inserted in an internal thread in the cylindrical screw. A hollow spring enveloping the locking device is used as an anti-rotation device or as an additional anti-rotation device. The clamp for clamping the rods of the external fracture fixation system can be a one-piece molded polymeric first and second jaw elements each having an axial bore therethrough. The jaw elements are connected on a first side of said axial bore by an integrally molded hinge element and each jaw element having a groove spaced from the axial bore on a second side thereof for receiving the rods.

By equipping the single-piece clamping elements with functionally different first and second clamping jaws, two clamping elements can be placed on top of one another each with their first clamping jaws, to form an articulation element in a simple manner.

BRIEF DESCRIPTION OF THE FIGURES

Now the invention is more closely described with reference to the drawings and with the aid of design examples:

FIG. 24 shows a perspective exploded view of an articulation element per a third design example of the invention, FIG. 25 shows a perspective illustration of an articulation element per a fourth design example when blocked with two clamped rod-shaped elements, FIG. 26 shows a top view of an articulation element per a fifth design example.

DETAILED DESCRIPTION

Figure 1:
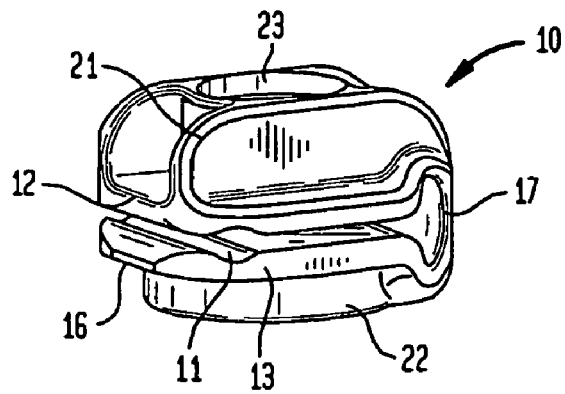
FIG. 1 shows a perspective view of a first design example of a clamping element according to the invention.

FIGS. 1 to 4 show a first embodiment of a clamping element 10 per the invention. FIG. 1 shows a perspective view at an angle from the top. The clamping element 10 has two opposing cavities and one cavity 11 to receive clamping jaws 12 and 13 forming a rod-shaped element. On their free ends 15, clamping jaws 12 and 13 each have a transversely running grooves 14, which together clamp to form the cavity 11. At the free ends 15, the outer edges 16 of the side facing clamping jaws 12 and 13 are slanted to simplify the lateral insertion of a rod-shaped element. Across from the cavity 11 and the free ends 15, a hinge 17 is arranged, connecting clamping jaws 12 and 13 in a single piece. When the clamping element 10 is intended for a rod with 4 to 6 millimeters in diameter, the opening at the free ends has a diameter of, for instance, 2 millimeters in a resting position.

When clamping element 10 is made of synthetic material, hinge 17 is a thinned material section, followed by a recess 18 running laterally and thus parallel to the cavity 11, which has a large radius of curvature on the side facing hinge 17 or, in other words, that the material cross section of hinge 17 increases only slowly. This can be seen particularly well in FIG. 2.

Figure 2:
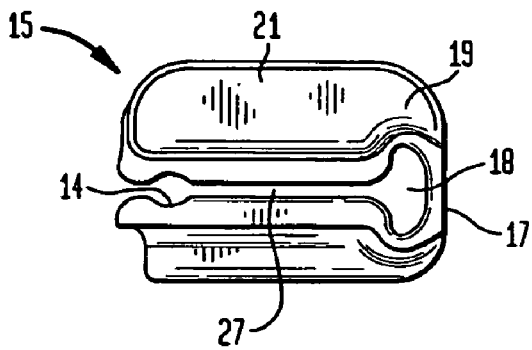
FIG. 2 shows a lateral view of the clamping element per FIG. 1.

FIG. 2 shows a lateral view of clamping element 10 per FIG. 1. When the material cross section is measured with reference to the radial direction of the curve, it will double up to an angle of 45 degrees. Up to an angle of 90 degrees, to wit, in the direction of the outside of clamping jaws 11 and 12, the material cross section will triple or sextuple. The latter material cross section has been referenced as 19 for clarification purposes. There is a slit 27 between the two clamping jaws 11 and 12, which shows a constant width, for instance in the resting position of clamping element 10. On both ends, slit 27 merges into the widening of grooves 14, respectively into recess 18.

Figure 3:
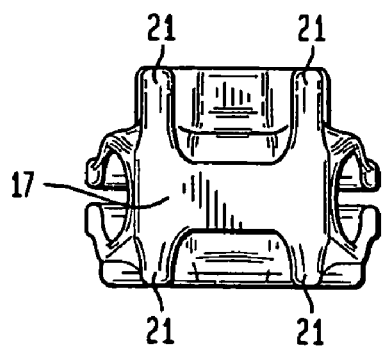
FIG. 3 shows a rear view of the clamping element per FIG. 1.

FIG. 3 shows a rear view of clamping element 10, i.e. of hinge 17. It is narrower than the width of the clamping jaws 11 and 12 in the area of free ends 15. The entire material cross section 19, as indicated above, exists only in the area of the cross ribs 21, which are particularly distinct in the figures in the upper area of the clamping jaw 12. There, the area between cross ribs 21 has been excluded with the exception of a round screw receptacle 23 in the top view. Screw receptacle 23, for instance, has a conical shoulder area or a step shoulder, whose purpose will be described later, which merges into a continuous bore in the top clamping jaw 12, which cannot be seen in FIG. 3.

Figure 4:
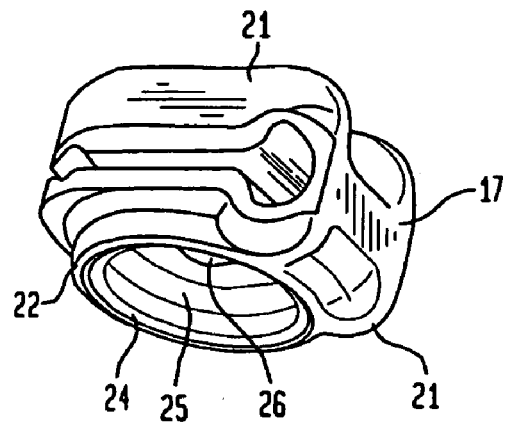
FIG. 4 shows another perspective view of the clamping element per FIG. 1.

Another perspective view of the clamping element 10 per FIG. 1 is illustrated in FIG. 4, this time at an angle from the bottom. In the lower clamping jaw 13 cross ribs 21 end in a ring flange 22, which, for instance, may have a flat recessed ring shaped step 24, where a weight and material saving recess 25 advantageous for injection molding can be connected, with a bore 26 in the center. This continuous bore 26 is aligned flush with the above-mentioned bore (reference 31 in FIG. 7) in top clamping jaw 12. At the clamping element 10, it runs vertically to the axis of the cavity 11 and parallel to the backside of hinge 17. However, it could also run at an angle. The bore 26 is cylindrical and in its interior, it has four guide ribs 32 arranged in regular intervals, illustrated in FIG. 7 and FIG. 30. Of course, three or five ribs 32, for instance, could be used as well.

Figure 5:
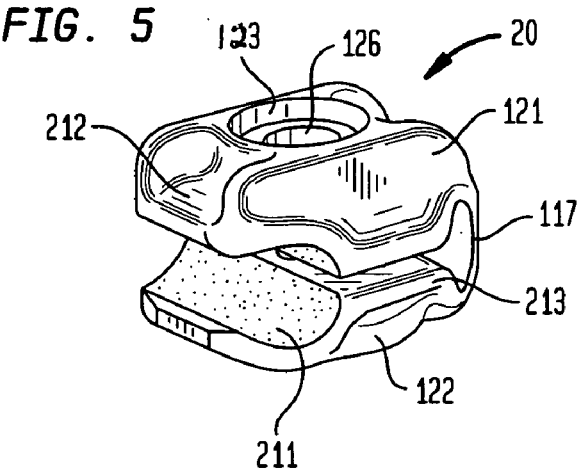
FIG. 5 shows a perspective view of a second design example of a clamping element according to the invention.

FIGS. 5 to 8 show a second embodiment of a clamping element 20 according to the invention with a bore 126, cross ribs 121, hinge 117, ring flange 122 and jaw 212. The same characteristics are identified with reference numerals having the same last two digits. FIG. 5 shows a perspective view, at an angle from above. The only difference between the two clamping elements 10 and 20 per FIG. 1 and FIG. 5 is that clamping element 20 is intended to receive a rod-shaped element larger in diameter. This means that the grooves 214 are larger. The center axis of cavity 211, however, is still at the same height of slit 27. Here, the grooves 214 are so large that the free ends 115 form only a rounded area 128 to the outside, which simplifies a lateral insertion of rods. Like the fender 129 the groove 214, respectively the recess 118, is spanned to ensure the rigidity of the clamping element 20 (or 10). If the clamping element 20 is intended for a rod with a diameter of 12 millimeters, the opening at the free ends has a diameter of, for instance, 9 millimeters in a resting position.

FIGS. 6 and 8 again show clamping element 20 in a lateral view, respectively in a perspective view at an angle from below.

Figure 7:
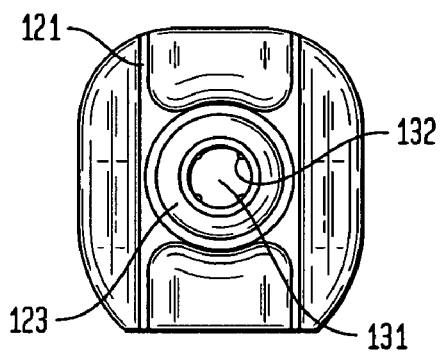
FIG. 7 shows a top view of the clamping element per FIG. 5.
Figure 6:
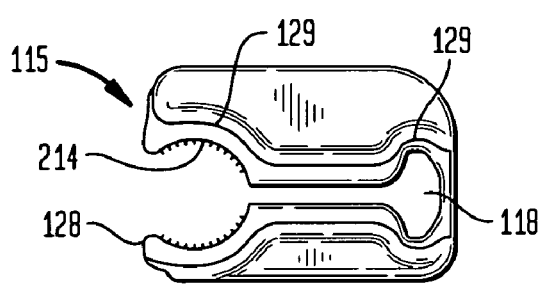
FIG. 6 shows a lateral view of the clamping element per FIG. 5.
Figure 8:
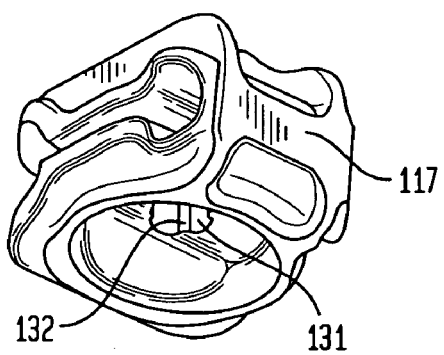
FIG. 8 shows another perspective view of the clamping element per FIG. 5.
Figure 30:
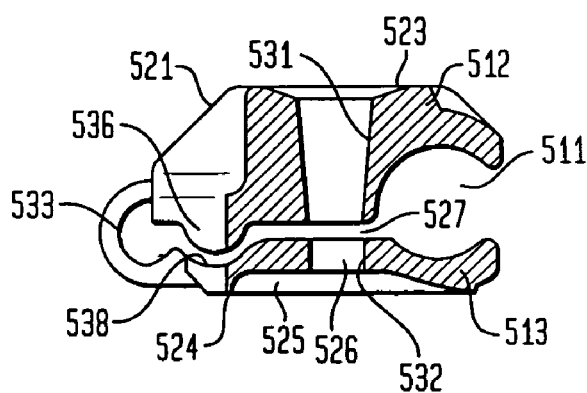
FIG. 30 shows a sectioned lateral view of the clamping element per FIG. 27.
Figure 31:
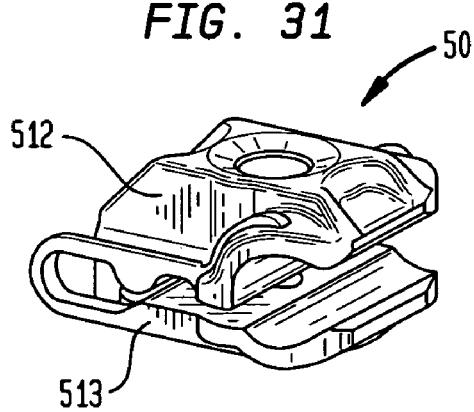
FIG. 31 shows a perspective view of the clamping element per FIG. 27.

FIG. 7 shows a view of clamping element 20 from above. Adjacent to conical shoulder 123 is a central continuous bore 131. The guide ribs 132 distinguishable here are a part of the interior wall of the bore 131. The bore 131 can be cylindrical as well; however, preferably it is conical, as illustrated in FIG. 30.

Figure 9:
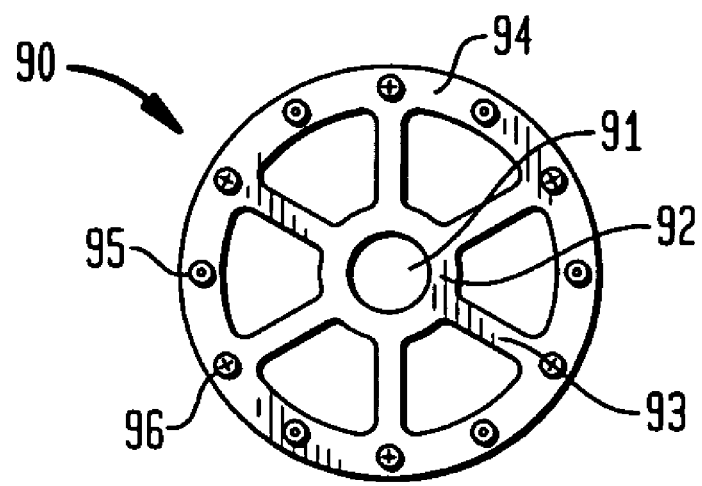
FIG. 9 shows a top view of an anti-rotation device for an articulation element per FIG. 11 below.
Figure 11:
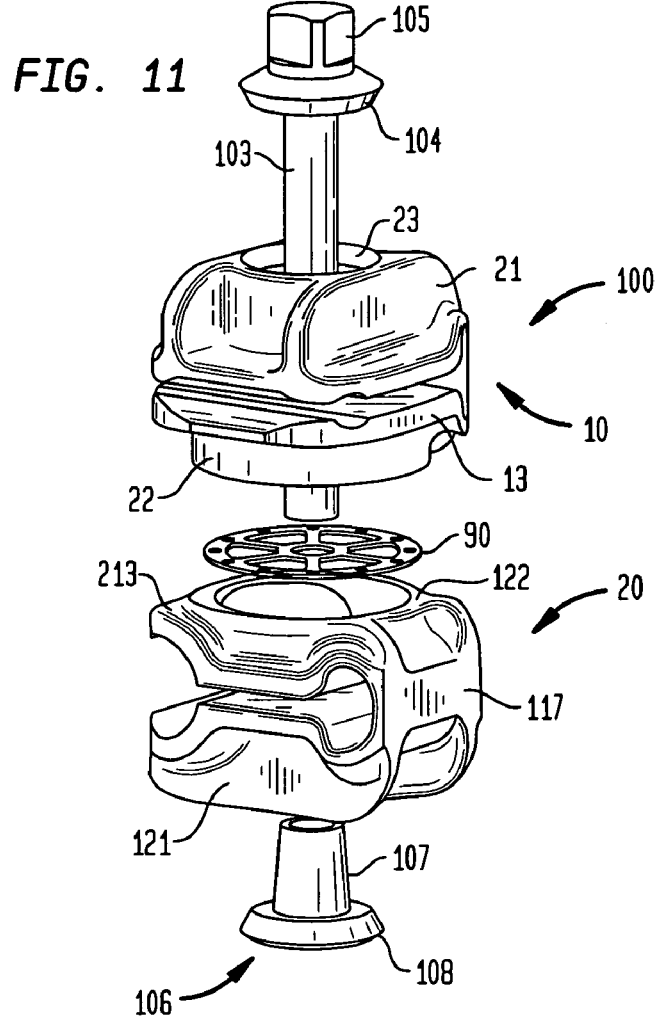
FIG. 11 shows a perspective exploded view of an articulation element per a first design example of the invention.

FIG. 9 shows a top view of an anti-rotation device 90 for an articulation element per FIG. 11. Anti-rotation device 90, for instance, is a thin metal plate with a central bore 91, a hub 92 and spokes 93. The outer rim 94, for instance, has successive punctured ridges 95 and recesses 96. For instance, they are arranged so that recesses 96 are always arranged opposite the six spokes 93 in this case, with each of the ridges 95 located intermittently.

Figure 10:
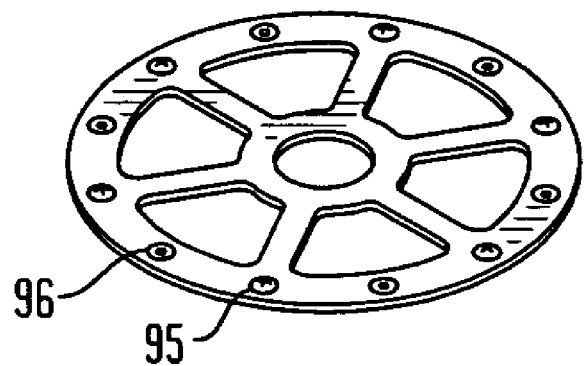
FIG. 10 shows a perspective view from the bottom of the anti-rotation device per FIG. 9.

FIG. 10 now shows this anti-rotation device 90 at an angle from below. It can be seen that ridges 95 are here in the area of spokes 93. This permits the utilization of a simple punching process to manufacture the plates of the anti-rotation device 90. Punctured ridges 95 and recesses 96 can be round, pyramidal or polygon shaped. They can run radially side by side in several rows, in a larger number than in FIG. 9 etc. In another alternate design, radial ribs can be used as well. If clamping elements 10, 20 have no recess 25, but only the step 24, the anti-rotation device 90 can also be a solid material plate with corresponding ridges/recesses. The importance of the function of the anti-rotation device 90 will be shown from the following description of a beneficial articulation element 100. Such an anti-rotation device 90 can also be achieved through the design of the material of the first clamping jaw 13.

Figure 12:
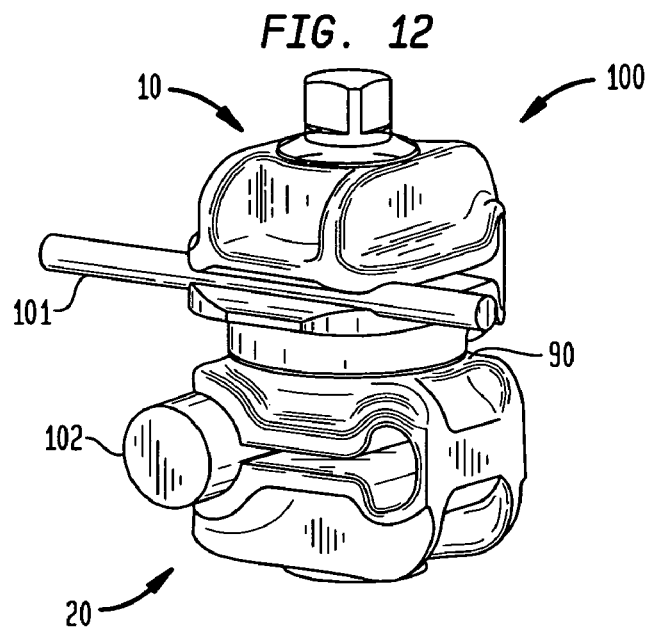
FIG. 12 shows a perspective illustration of the articulation element per FIG. 11 when blocked with two clamped in place rod-shaped elements.

FIG. 11 shows a perspective exploded view of a preferred articulation element 100 according to a first embodiment of the invention. FIG. 12 shows articulation element 100 per FIG. 11 in a blocked state with two clamped rod-shaped elements 101 and 102. The rod-shaped element 101 is a small diameter connector and the rod-shaped element 102 is a larger diameter fastening rod. Articulation element 100, on the preferred embodiment, is comprised of five parts. These are two identical clamping elements 10 or 20 or one clamping element 10 each for a smaller rod-shaped element 101 and a clamping element 20 for a larger rod-shaped element 102. These are positioned with their sides with the flange 22, 122 facing each other. The anti-rotation device 90 is arranged between these two flanges 22 and 122.

Through the then aligned bores 31, 131, 91 and 26, 126 a screw 103 is inserted, which can sit on the conical screw receptacle 23 with its conical flange 104. For tightening, screw 103 for instance has a square drive head 105. It is clear that instead of a square, a hexagon or a slit etc. can be utilized. Preferably, the shoulder 104 is designed to be complementary to the receptacle 23, 123. A nut 106 is attached from the other side. The nut 106 has a slightly conical sleeve 107 and a conical flange 108 as a covering cap. The shape of flange 108 corresponds to the shape of screw receptacle 23, 123 of clamping element 10 or 20. The sleeve 107 is inserted in bore 131 and, to the best advantage, protrudes into bore 126 and/or through it. The sleeve 107 is fitted in the press fit; additionally, it can also have an external thread. It can be designed as a fit for one of the internal threads used in bore 26, 126.

Figure 15:
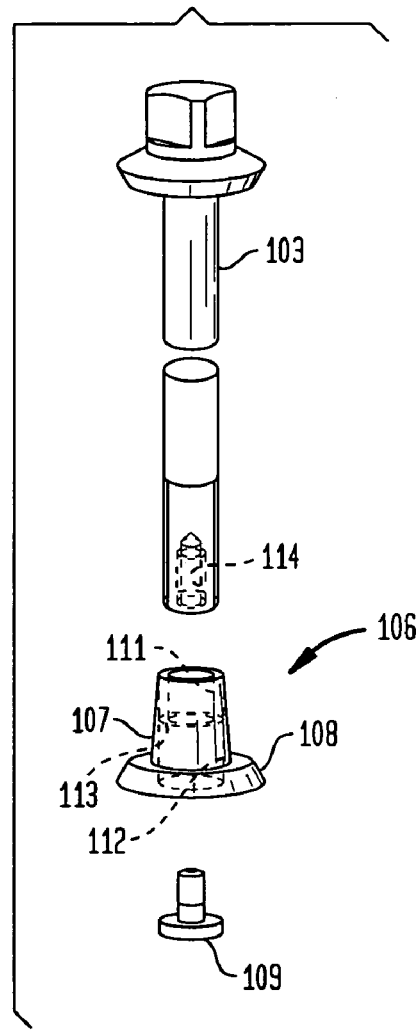
FIG. 15 shows a partially sectioned lateral view of a part of a locking screw, a nut and a self-locking bolt for an articulation element per one of the FIGS. 11 to 14.

In another design version, not illustrated in the drawings, a clamping element is equipped with a tilting, but torsion rigid, bearing for the nut. The clamping jaw 12 again has the conically opening bore 31. This bore 31, however, has a recess on the side facing away from the cavity 11, which can be a rectangular slit in particular. During the assembly, the cylindrical nut is inserted in the recess. Otherwise, the fastening can be designed as illustrated in FIG. 15. A tolerance exists through the cylindrical nut, so that when a rod 102 is clipped into cavity 11 the top part 12 of the clamping element can be tilted as well. In order to ensure the fixation of screw 103 and to design the nut torsionally rigid, it has an appendage or projection, which protrudes into the said recess with lateral tolerance. In a lateral view of the clamping element, the projection has a tolerance in the recess to permit the tilting motion of top part 12. In addition to the nut with projection, other design versions are possible, for instance, an L-shaped flattened nut, which, for example, has wobble rivets and is punched, so that an appendage protrudes into a corresponding nut in top part 12 and produces the torsion rigidity.

The nut 106 has an internal thread that fits the complementary external thread of screw 103.

FIG. 12 then shows the assembled articulation element 100 with a clamping element 10 for a thin rod 101 and a clamping element 20 for a thicker rod 102. Through the tightening of screw 103 opposite nut 106, the two clamping elements 10 and 20 are pulled together, since the forces exerted by hinges 17, 117 move the two lower clamping jaws 13, 213 of the clamping elements 10 or 20 towards one another.

Then, by exerting pressure, a rod 101 or 102 can be inserted laterally in the respective cavity. Since the diameters of rod 101 or 102 are larger than the opening at the free ends 15, 115 it is protected from falling out. Through a roughening of grooves 14, 214, not illustrated in the drawings, it is also protected from a simple longitudinal displacement.

The two hinges 17, 117 also exert pressure on anti-rotation device 90, so that clamping elements 10 or 20 themselves are protected from a slight rotation against each other around the axis of screw 103. The ridges 95 press themselves, i.e. according to the description of FIGS. 9 and 10, in both directions vertically to the plate level into the ring-shaped step 24. This protects each of clamping jaws 13, 113, and, with that, clamping elements 10 or 20 from a slight twisting.

If screw 103 is tightened further, clamping jaws 12, 212 and 13, 213 are moved closer towards one another against the resetting force of hinges 17, 117 and are finally completely blocked in their angled position through the use of the plate of anti-rotation device 90 placed between the clamp elements. At the same time, this fully secures the rods 101 and 102 in grooves 14, 214 against longitudinal displacement as well as against twisting by minimizing the cavity 11, 211. While self-locking screw 109 is illustrated only in connection with FIG. 13, it can be utilized here as well. Preferably the nut 106 is designed as a continuous sleeve.

When screw 103 is opened, nut 106 remains in the one clamping element. The anti-rotation device 90 has impressed itself into the softer material of step 24. This impression makes it preferable, with the exception of an immediate tightening of the screw in this or another place for the same patient to provide an external fixator clamping element which is for a single use by a patient—i.e. use of the clamping element only once and throwing it away after use. The material used for the clamp may be PEEK (Poly Ether Ether Ketone), and may have chopped carbon fiber reinforcement for extra strength. This allows a one-piece polymeric clamp to be injection molded. The pressed in traces of the anti-rotation device in the step 24 is a sign of use for the clamping element, so that the user can see that the reuse of the product can be excluded.

Figure 13:
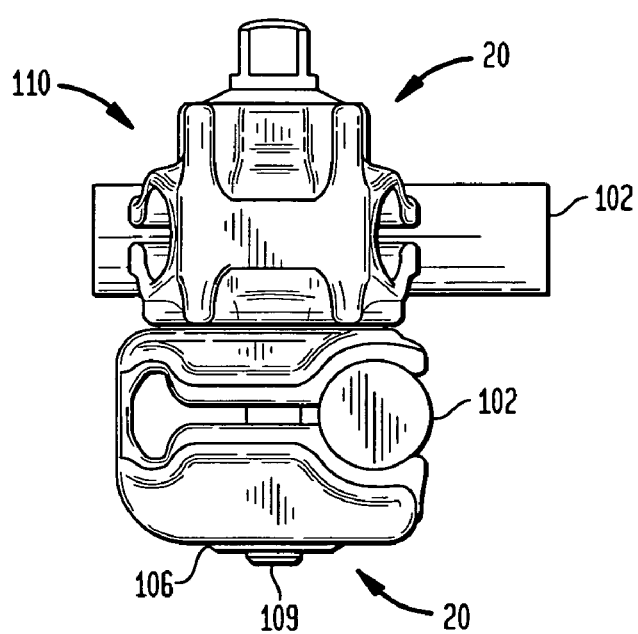
FIG. 13 shows a lateral view of an articulation element per a second design example of the invention when blocked with two clamped rod-shaped elements.

FIG. 13 shows a lateral view of an articulation element 110 according to a second embodiment of the invention in blocked condition with two clamped thick rod-shaped elements 102. Therefore, two clamping elements 20 per FIG. 5 have been utilized in this design example.

Figure 14:
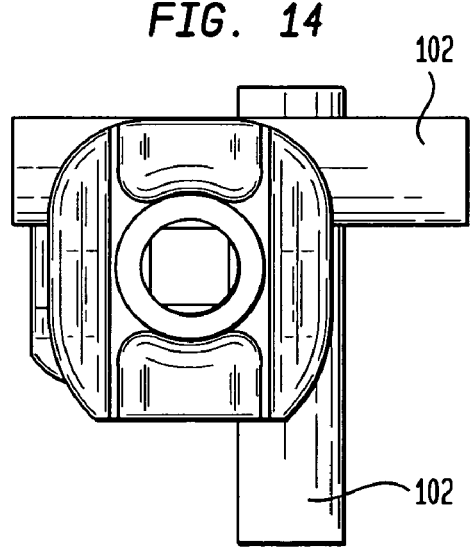
FIG. 14 shows a top view of the articulation element per FIG. 13.

FIG. 14 shows a top view of the articulation element per FIG. 13, where two rods 102 have been arranged twisted to one another at a 90-degree angle.

FIG. 15 shows a partially sectioned side view of a self-locking screw 103, a nut 106 and a self-locking screw 109 for an articulation element 100, 110 according to one of the FIGS. 11 to 14. The cone 107 of the nut 106 can be smooth; however, it can also have a thread. Then bore 31 is preferably equipped with a thread as well. The sleeve of nut 106 has a continuous bore with a first narrower section 111, with an internal thread to receive the external thread of screw 103. A connected broad second section 112 has a shoulder 113, where the screw head of the self-locking screw 109 can sit. Self-locking screw 109 is intended to screw into an internal thread 114 in the tip of screw 103. For this purpose it can be used in particular, for instance with glue or another material, so that after a prior assembly of an articulation element 100 or 110, the self-locking screw 109 cannot be loosened from the thread 114 anymore, thereby ensuring the unity of articulation element 100 or 110.

FIGS. 16 to 19 show a third design example of a clamping element 30 according to the invention in a perspective view, a top view, a rear view and another perspective view. The difference between the first two design examples and the ones now following is that hinge 17, 117 are connected directly to the body of clamping jaws 12 respectively 13 in the first two design examples and directly passes into ribs 21, 321. Clamping jaws 12, 212 respectively 13, 213 are connected to one another on the entire backside of clamping element 10 or 20.

In the clamping element 30, the two clamping jaws 312 and 313 are connected only via two lateral connecting bars 333. The connecting bars 333 each include a lower short transition bar 334 (434 of clamping element 40) into lower clamping jaw 313 and a long bar 335, running parallel to upper clamping jaw 312, before it merges into upper clamping jaw 312 in the area of the wall 341 of cavity 311. A dividing slit 339 is located between each of the two connecting bars 333 and the upper clamping jaw 312, so that the two opposing elements 336 and 338 are separated from the upper or lower clamping jaw 312 or 313. On the upper clamping jaw 312, a semi-cylindrical portion 336 is included, opposite a complementary groove 338 at a distance corresponding to, for instance, half or one third of the height of slit 327. Semi-cylindrical portion 336 of jaw 30 and 436 of clamping element 40 and complementary groove 338 are divided in the center by a slit 337 (slit 437 of clamping jaw 40) in two sections each separate from one another. The illustrated design examples can also be designed without slit 337, so that a semi-cylindrical portion 336 and a groove 338 are located opposite one another. Then the bearing is not divided in the center. It is not necessary that a clamping element has a receptacle for an anti-rotation device according to the third or fourth design example.

The other characteristics of lower clamping jaw 313, i.e. the receptacle 324 and 424 of clamping jaw 40 for anti-rotation device 90 and bore 326 with the guide ribs 332 and 432 of clamping element 40, and upper clamping jaw 312, i.e. the receptacle 323 and 423 of clamping element 40, the conical bore 331 (and bore 431 of clamping jaw 40) and the ribs 321 can be designed in the same manner as in the first two and the last design embodiment. For ribs 321, one difference is that they represent a direct extension of hinge 17 for clamping elements 10 and 20. For the clamping elements 30 and 40 hinges are formed through connecting bar 333, 433 in a resting position, which is connected only indirectly to the ribs 21 via the wall 341, 441 of cavity 311, 411.

FIGS. 20 to 23 show a fourth design example of a clamping element 40 according to the invention in a perspective view, in a top view, in a lateral view and in another perspective view. Here, cavity 411 is designed large to receive a thick rod-shaped element 102. In the FIGS. it can be seen how the long upper bar 335, 435 merges into wall 441 and, in almost a quarter circle, remains spatially separated from the rib 321, 421.

FIG. 24 shows a perspective exploded view of an articulation element 120 according to a third embodiment of the invention. FIG. 25 shows a perspective illustration of an articulation element 130 according to a fourth embodiment in a locked condition with two clamped thin rod-shaped elements 101, and FIG. 26 shows a top view of an articulation element 140 according to a fifth embodiment. The structure of these articulation elements 120 and 130 corresponds to the one of the first two design examples of the articulation elements 100 and 110. If two equally strong rod-shaped elements 101 or 102 must be clamped, the same two clamping elements 30 or 40 are used, with the lower clamping jaws 313, 413 opposite one another. Another anti-rotation device 90 is again located between these clamps. For different clamping strengths one clamping element 30 and one clamping element 40 each are used.

In the resting position of the clamping elements 30, 40, 50, 60 and 70, clamping jaws 312, 412, 512, 612, 712 and 313, 413, 513, 613, 713 are held by the spring force of the two lateral bars 333, 433, 533, 633, 733 at the distance of the slit 327, 427, 527, 627, 727. When screw 103 is tightened, the slit is minimized. Through the central transfer of force via the screw and nut elements 104 and 108 on the identical areas 323, 423, the slit 327, 427 is minimized in its thickness until the groove 314, 414 contacts the rod 101 or 102 in the cavity 311, 411, 511, 611, 711, 911. Then the (upper) clamping jaw 312, 412, 512, 612, 712 with the ribs 321, 421, 521 deviates around the rod 101 or 102 and the semi-cylindrical region 336, 446 touches down on the complementary area 338, 438, 538, 638, 738. When screw 103 is tightened further, the blocking effect sets in as of this time and the unit semi-cylindrical region 336, 436, 536, 636, 736—complementary area 338, 438 takes over the hinge function of bar 333, 433 and avoids too much stress on the same.

Figure 32:
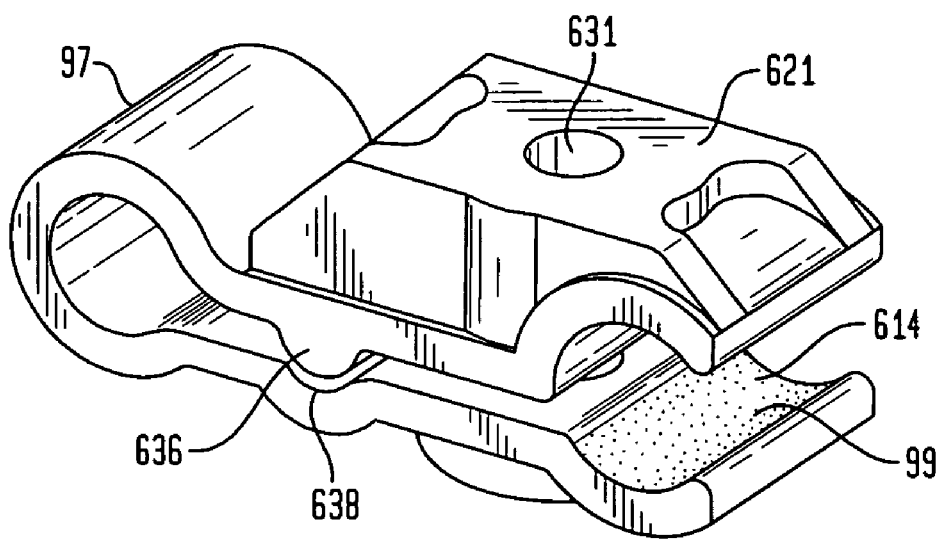
FIG. 32 shows a perspective view of a clamping element according to a sixth design example per the invention.
Figure 33:
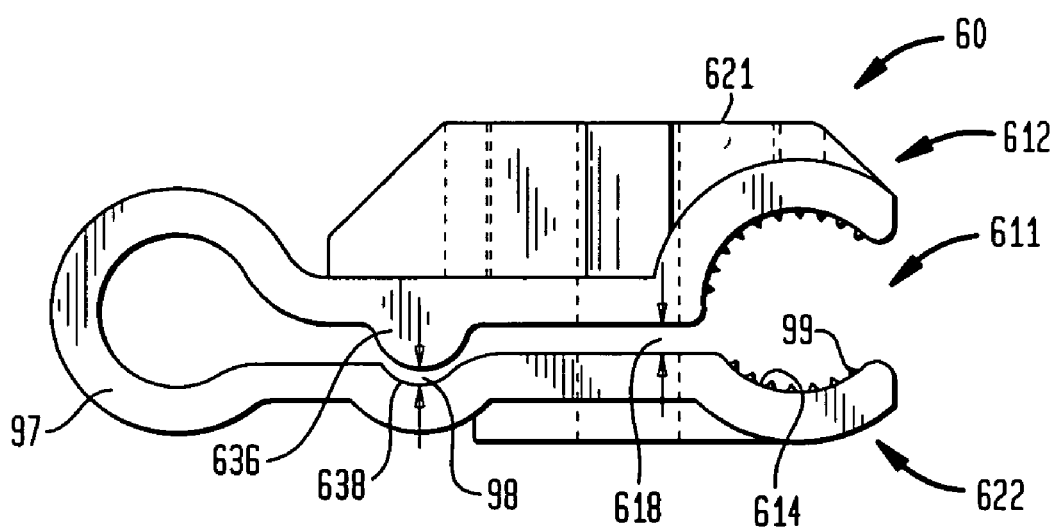
FIG. 33 shows a lateral view of the clamping element per FIG. 32.

For instance, this can also be solved as shown in FIGS. 32 and 33, which will be described later.

FIGS. 27 to 31 show a clamping element 50 according to a fifth design example per the invention, in a bottom view, a lateral view, a top view, a sectioned lateral view and in a perspective view. This clamping element 50 is intended for use with a large diameter rod-shaped element 102. Of course, it can also be modified so that it can receive a smaller diameter rod-shaped element 102. Clamping element 50 has a lower clamping jaw 513, a ring shaped step 524, a recess 525, a slit 527 and pivot bearing 542. An important difference between the clamping element 40 (or 30) and clamp 50 is that the upper long bars 535 go off directly from the body of clamping jaw 512 and with that limit the outer edge of clamping element 50. The bars 535 in particular are not shaped as ribs on wall 541 of cavity 511. The semi-cylindrical portion 536 and complementary groove 538 are not separated by a slit 337, 437. The semi-circular passages of the long bars 535 and short transition bars 534 into the semi-cylinders 536 and complementary groove 538 are wider and extend over them by the entire radius of the passage. The short transition bar 534 here includes a passage step 542, which corresponds to almost the material thickness of the bar 533. The bar 533 is here, as in the other design examples, for instance between 1 and 5, preferably between 2 and 3 millimeters thick. The design of bores 526 and 531, which can be seen in the cross section of FIG. 30, can have the following dimensions. A cylindrical bore 526 in the lower clamping jaw 513 has a diameter of 6.5 millimeters, with the ribs 532 minimizing the diameter to 5.8 millimeters. The conical bore 531, for instance, has an angle between 5 and 10, and preferably 8 degrees, and assumes a diameter of 8.5 millimeters in depth. The angle of the conical screw receptacle 523, for instance, is between 45 and 75, preferably 60 degrees; the height for instance is 2 millimeters.

FIG. 32 shows a perspective view of a clamping element 60 according to a sixth design example per the invention, with FIG. 33 showing a lateral view of this clamping element 60. The clamping element 60 has a top surface 621 with a bore 631. This design example also shows the arrangement of non-skid elements 99. They are pyramidal ridges at regular intervals on the surface of the groove 614. These ridges 99 can also be designed in a nub shape. It is important that they protect particularly the thicker rod-shaped elements 102 from twisting or longitudinal slipping in the clamp.

The sixth design example per FIGS. 32 and 33 has the semi-cylindrical portion 636 and the groove 638. As mentioned previously, these elements can also be located across from one another. It is important that the hinge element 97 has a smaller distance 98 upon its passage into the clamp halves 612 and 622 than at 618 close to cavity 611. The distance 618 is substantially greater than the distance 98. This ensures that upon the tightening of a screw and the closing of the clamping jaws the distance 98 first reduces to zero, so that the load of the clamping from this time on is taken over by the contact point or the contact line of the complementary elements 636 and 638 and the deviating axis is moved into this contact line. With that, the spring action is converted and effectively increased.

Hinge element 97 in the sixth design example is a resilient almost closed cylinder at a distance behind the contact line. It opens particularly to the top, so that it does not protrude over the underside of clamp half 622 of clamping element 60.

Figure 16:
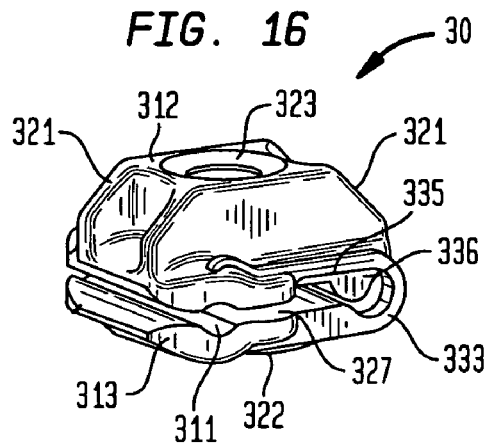
FIG. 16 shows a perspective view of a third design example of a clamping element per the invention.
Figure 18:
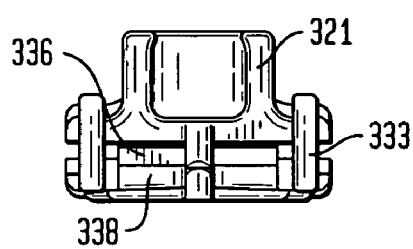
FIG. 18 shows a rear view of the clamping element per FIG. 16.
Figure 17:
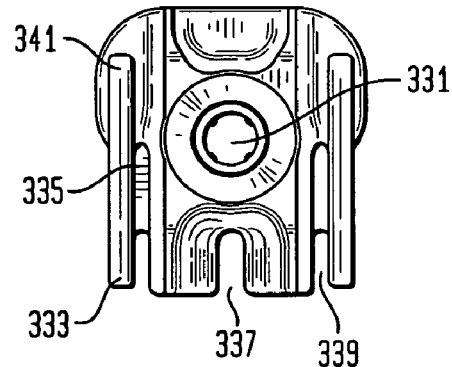
FIG. 17 shows a top view of the clamping element per FIG. 16.
Figure 19:
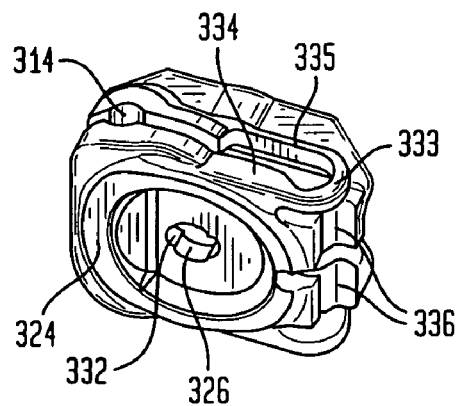
FIG. 19 shows another perspective view of the clamping element per FIG. 16.
Figure 20:
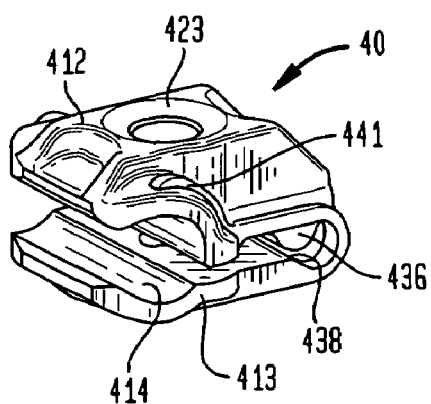
FIG. 20 shows a perspective view of a fourth design example of a clamping element per the invention.
Figure 21:
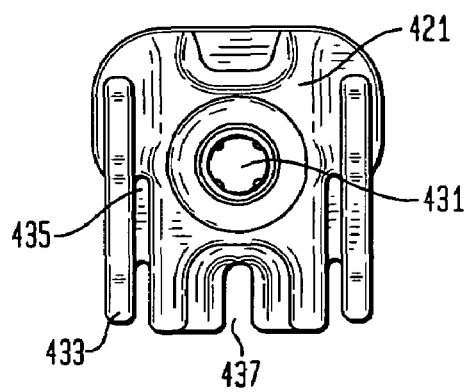
FIG. 21 shows a top view of the clamping element per FIG. 20.
Figure 22:
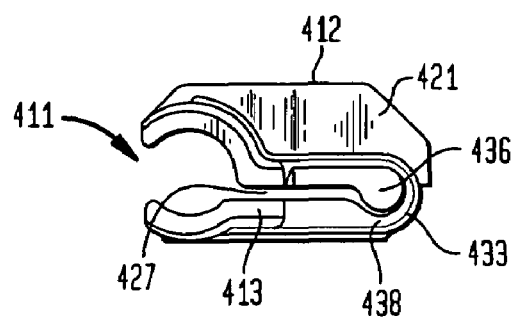
FIG. 22 shows a lateral view of the clamping element per FIG. 20.
Figure 23:
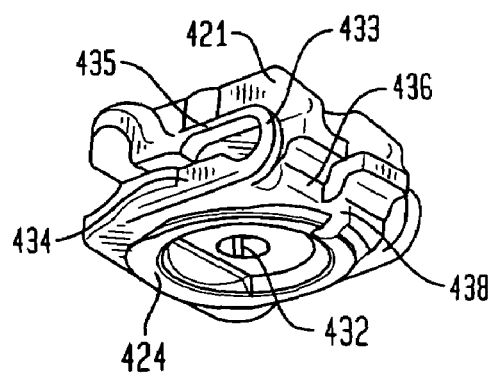
FIG. 23 shows another perspective view of the clamping element per FIG. 20.
Figure 27:
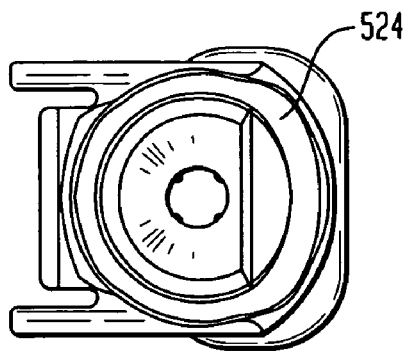
FIG. 27 shows a bottom view of a clamping element per a fifth design example according to the invention.
Figure 28:
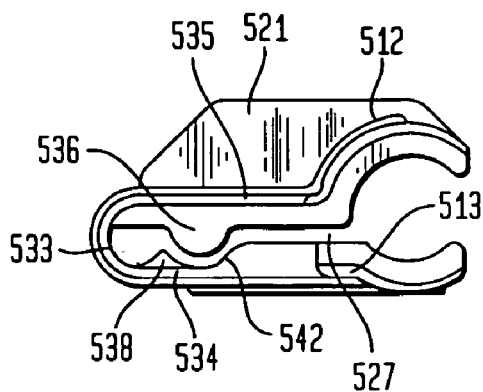
FIG. 28 shows a lateral view of the clamping element per FIG. 27.
Figure 29:
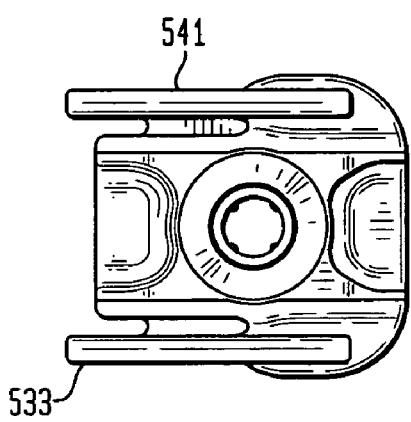
FIG. 29 shows a top view of the clamping element per FIG. 27.
Figure 34:
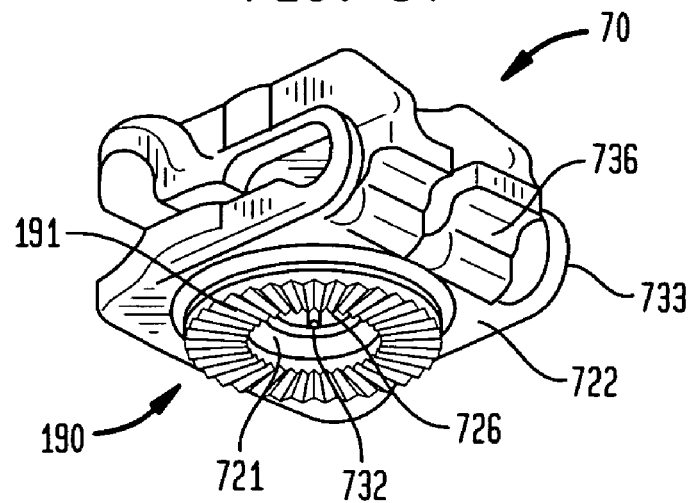
FIG. 34 shows a perspective view of a clamping element according to a seventh design example of the invention in a variation of the element per FIG. 16.

FIG. 34 shows a perspective view of a clamping element 70 according to the seventh design example per the invention in a variation of the element per FIG. 16.

Figure 35:
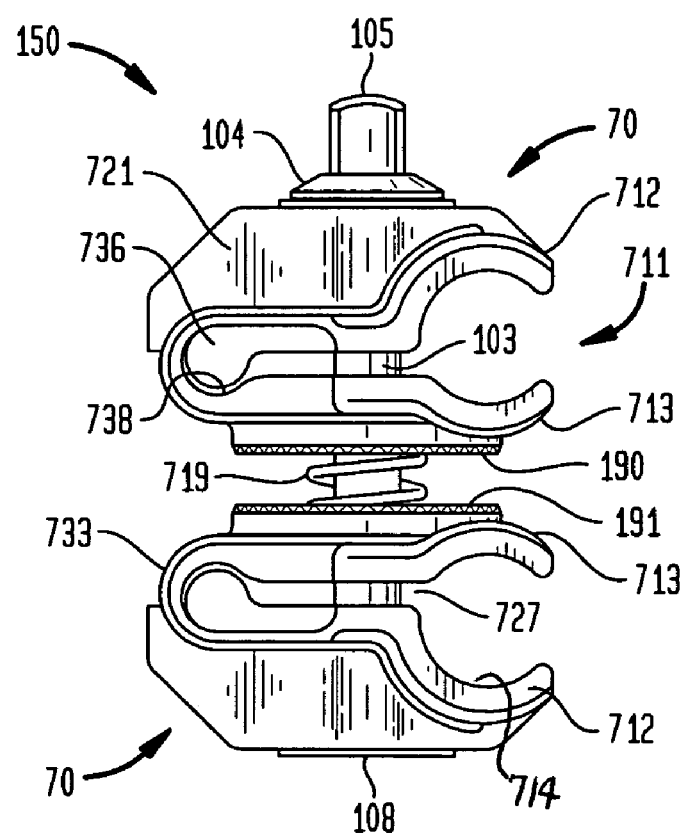
FIG. 35 shows a lateral view of an articulation element according to a sixth design example of the invention, constructed with two clamping elements per FIG. 34.

FIG. 35 shows a lateral view of an articulation element 150 according to a sixth design example of the articulation element of the invention, consisting of two clamping elements 70 per FIG. 34. The anti-rotation device 190 is comprised of radial prisms 191 arranged at one level on face 722, with the continuous bore 726 in the center with ribs 732. In another design version, the radial prisms 191 can also be arranged conically, so that with the complementary prisms 191 in a second clamping element a self-centering articulation element 150 is created. The design example illustrated in FIGS. 34 and 35, however, has the advantage that the two anti-rotation devices 190 of identical clamping elements 70 can directly engage in one another.

For the articulation element 150 per FIG. 35, a spiral or coil spring 719 is arranged between the two clamping elements 70, which is supported by the spring receptacle 721. The spring receptacle 721 can form a hemispherical area as in FIG. 34; it can also be level and smooth; in particular, it can be rough to ensure a greater resistance of the spring 719 against twisting. The spring 719 pushes the two clamping elements 70 away from one another and is intended to secure the twisting of the two clamping elements 70 against one another. It does not secure the forcing apart of the jaws 712 and 713; for this purpose the resilient hinges 733 and 97 are intended, which open against the forces acting upon the clipping in of the rods 101 and 102 in a radial direction with respect to grooves 714. The spring 719 can also be a disk spring package or another resilient element.

Figure 36:
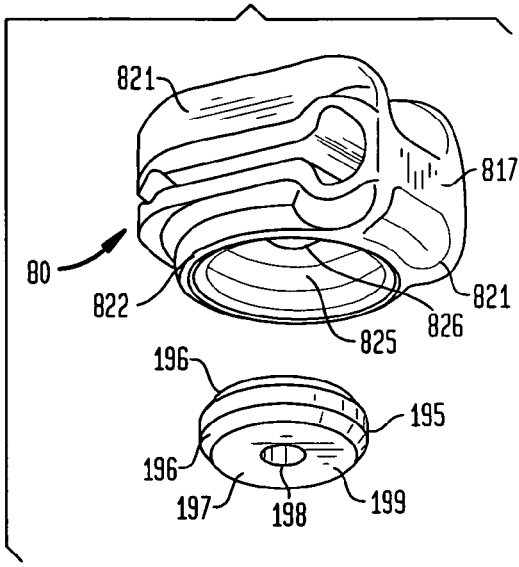
FIG. 36 shows a perspective view of a clamping element according to an eighth design example per the invention for the utilization of another anti-rotation device for an articulation element.

In particular, it can also be a flexible synthetic foam element 199 as per FIG. 36. Only upon the tightening of screw 103 the anti-rotation devices 190 interlock and determine the angle position of the articulation element 160 as per FIG. 37.

FIG. 36 shows a perspective view of another anti-rotation device 199 for an articulation element in interaction with an eighth design example of a clamping element 80 equipped for this purpose. This is a flexible cylindrical element 199 with a central bore 198 for receiving screw 103. It can be used in the place of an anti-rotation device 90. The advantage is that its material on the bottom and lid surfaces 197 is harder and, in particular, can also be structured or span hard inserts to engage in the ring-shaped step 824. Clamping element 80 has a bore 826, a recess 825, a ring flange 822, cross ribs 821 and a hinge 817. The clamping element 80 is designed here according to the design example per FIG. 1, only the depth and the sidewalls 822 are intended to receive the anti-rotation device 199. In the cylinder area, the element 199 is flexible to be compressed when screw 103 is tightened. In doing so, the undersides of the clamping element 80 of an articulation element 160 per FIG. 37 might touch. The anti-twisting device is beveled and has conical slants 196 between the surface 195 and the lid or the floor area 197.

It is advantageous that the material in the floor and lid area of the anti-rotation device 199 is harder than the material of the clamping elements utilized, and in the solid material preferably consists of a flexible, compressible material, particularly synthetic foam.

Figure 37:
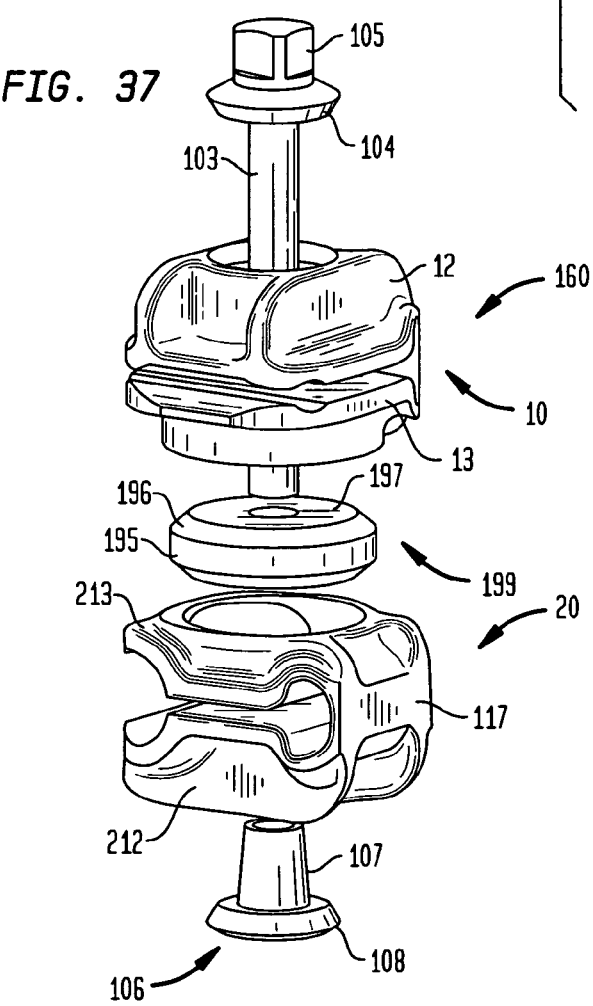
FIG. 37 shows a perspective exploded view of an articulation element according to a seventh design example of the invention.

FIG. 37 shows a perspective exploded view of an articulation element 160 according to a seventh design example of an articulation element of the invention.

Figure 38:
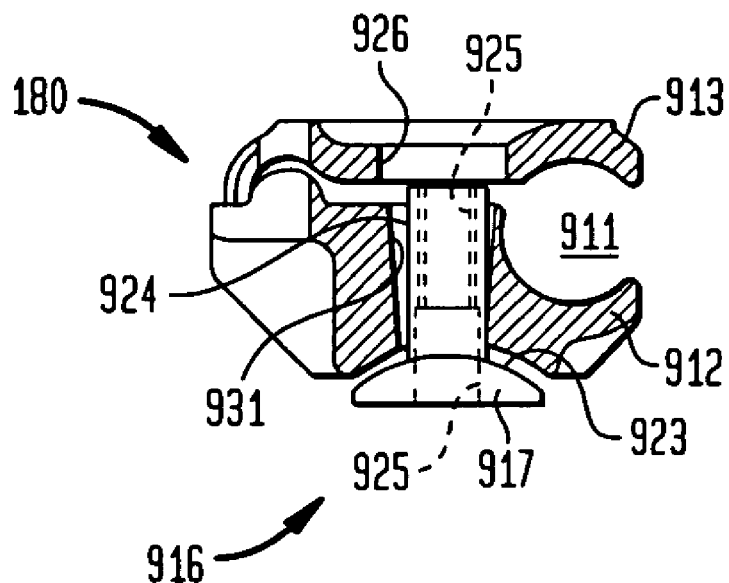
FIG. 38 shows a lateral view of a clamping element according to a ninth design example per the invention.
Figure 39:
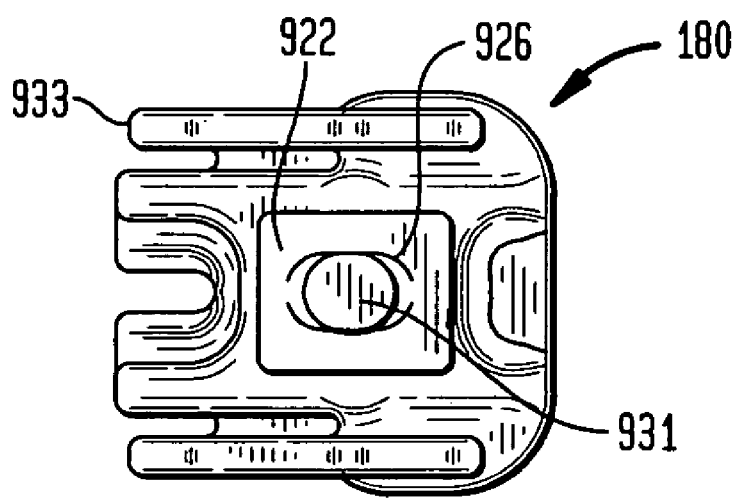
FIG. 39 shows a top view of the clamping element per FIG. 38.

FIG. 38 shows a lateral view of a clamping element 180 according to a ninth clamp design example per the invention with a related nut 116, and FIG. 39 shows a top view of the clamping element 180 per FIG. 38. Bore 926 in the clamping jaw 913 has a greater diameter than in the other previously mentioned design examples. The bore 931 in the clamping jaw 912 is slightly conical, with the smaller diameter in the area of the outer port, which can be better seen in FIG. 39. The port ends in the nut head receptacle 922, which is preferably hemispherically concave, with the ball diameter approximately corresponding to the lower radius of curvature of the backside of the nut head 923 of the nut head 917 of nut 916. Nut 916 has a cylindrical sleeve 924, which has an internal bore and has an internal thread 925 to receive the fastening screw 103. The bore of the sleeve 924 can be continuously equipped with a smaller diameter 925 to receive the self-locking screw 109 per FIG. 15.

It is important that nut 116 with its head 117 in the receptacle 922 is movable against the clamping element 180, in a similar manner as screw 103 with its clamping element. This simplifies the clipping open of rods 101 or 102, particularly of thick rods 102. The nut head receptacle 122 in the area of the port of bore 931 is designed asymmetrically, i.e. the spherical recess has an oblong design in two opposite directions according to the reference 926 and corresponds to an oval or elliptical receptacle, so that nut head 917 cannot twist with respect to clamping element 180. Thus, with the determination of the orientation of the jaws 913 and 912 for the axes to receive the rods, it can be ensured that nut 916 does not over rotate when screw 103 is tightened. On the other hand, nut 916 permits the tipping of the clamping element 180 opposite its position, as does the opposite screw 103 for the related clamping element.

The diameter of the anti-rotation device 90 of FIG. 9 is 30 millimeters and the contact surface (radial width) for the outer rim 94 is 3 millimeters. Instead of placing the ridges on element 90, the structures (ridges) can also be integrated in the material of the clamping jaw 13, for instance radial grooves.

The ribs 21 through 821 of clamping jaws 12 through 812 are intended particularly for the purpose of introducing half the force in vertical direction, i.e. lengthwise to screw 103, as a pressure force into the spring element, i.e. hinge 17-817 or 33-933.

Instead of semi-cylindrical portion 336-736 and complementary groove 338-738, level opposing areas can be utilized as well. These opposing areas should be arranged only in the resting position of the clamping element at a distance from one another at less than the slit distance 27-727. Complementary deviation stops 336-736, 338-738 in this sense are also two raised ribs on clamping jaws 12-912 and 13-913, since these also form a pivoting lever. With that, the hinges of the third and fourth design example have been divided in resilient bars 33-933, 34-534 and 35-535 as well as pivoting lever forming stop media 336-736, 338-738. Such deviation stops can also be used in for the clamping elements of the first, second and fifth design examples.

Instead of a screw 103, another locking device can be used, for instance a clamping lever or a bayonet catch.

It is emphasized that the term design example in the previously mentioned description does not mean that only the elements described with respect to the respective clamping element or articulation element are subject of the invention. In particular, these are also combinations of the characteristics described in objects of various embodiments and FIGS. For instance, a clamping element is an object of the invention, which has the bore and nut per FIG. 38, the wide spring braces 33 per FIGS. 27 to 31, a counter nut 109 per FIG. 15 and non-skid elements 99 for the rods per FIG. 32 or a part thereof. A corresponding articulation element can be comprised of any two random above-mentioned clamping elements, if they can be utilized for the selected anti-rotation device.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A one-piece clamping element comprising two opposing first and second clamping jaws forming a laterally open cavity to receive a rod-shaped element and at least one internal hinge arranged opposite the cavity connecting the two opposing clamping jaws to one another and thereby making them movable towards and away from one another, with each clamping jaw having a bore aligned with one another, wherein the hinge is resilient and that the bores are arranged between the cavity and hinge wherein the hinge includes two resilient lateral bars, which each merge into the first and second clamping jaws wherein the lateral bars include a resilient and primarily C-shaped portion on the side of the clamping element opposite the cavity, each of which merges into the first and second clamping jaws wherein each bar has engagable part-cylindrically-shaped protrusion and complementary groove acting as stops, which allow a pre-determined distortion about an axis of the resilient lateral bars before the stops come into engagement.

2. The clamping element as set forth in claim 1, wherein a first clamping jaw has an anti-rotation device on its exterior or a receptacle for receiving an anti-rotation device.

3. The clamping element as set forth in claim 1, wherein the hinge includes a resilient hinge wall, which merges into two parallel ribs formed on said first and second clamping jaws, which ribs run past the bore and which end in an area of a free end of at least one of the clamping jaws or which merge into the body of the one clamping jaw.

4. The clamping element as set forth in claim 1, wherein the lateral bars include a semi-circular centerpiece, followed at one end by a first bar portion having an end integral with a first side of the first clamping jaw and followed at a second end by a second bar portion integral with a first side of the second clamping jaw, the second bar portion longer than the first bar portion.

5. The clamping element as set forth in claim 4, wherein the longer bar is in the area of a wall adjacent to the cavity and is connected with the second clamping jaw in the form of a rib.

6. The clamping element as set forth in claim 1 wherein the lateral bars are separated laterally from the clamping jaws by a slit.

7. The clamping element as set forth in claim 1 wherein the lateral bars include a resilient and primarily C-shaped portion on the side of the clamping element opposite the cavity, each of which merges into the first and second clamping jaws wherein each bar has an engagable part-cylindrically-shaped protrusion complementary and groove acting as stops, which allow a pre-determined distortion about an axis of the resilient lateral bars before the stops come into engagement.

8. The clamping element as set forth in claim 1 wherein the bore in the first clamping jaw is cylindrical and has a longitudinal alignment rib.

9. The clamping element as set forth in claim 8 wherein the bore in the second clamping jaw conically narrows in the direction of the first clamping jaw and has an enlarged diameter step to receive the head of a screw or a nut.

10. The clamping element as set forth in claim 9 wherein the bore has a lateral recess for receiving an anti-rotation device of the nut.

11. An articulation element having first and second clamping elements as set forth in claim 1, which clamping elements are arranged on top of one another with their first clamping jaws adjacent one another, and having an at least two-piece locking shaft with a first part of the locking shaft insertable through a bore of the second clamping jaw the first clamping element, and with a second part of the locking device insertable through a bore of the first clamping jaw of the second clamping element, and with one or the other or both parts being able to be brought in contact with one another through the bores in the first clamping jaws, and where the first and second clamping jaws of the first and second clamping elements can be blocked with the locking device.

12. The articulation element as set forth in claim 11, wherein an anti-rotation device is arranged between the first clamping jaws that are arranged on top of one another, the anti-rotation device having a central bore.

13. The articulation element as set forth in claim 12, wherein the anti-rotation device is a plate whose material is harder than the material of the clamping elements and which has ridges formed on both sides of the plate.

14. The articulation element as set forth in claim 12, wherein the anti-rotation device is a cylinder whose material in a floor and a lid area is preferably harder than the material of the clamping elements, and which consists of a flexible, compressible material in the solid material part, in particular synthetic foam.

15. The articulation element as set forth in claim 11, wherein the locking device includes a cylindrical screw and a conical nut, and that the conical nut preferably has a stop shoulder for a self-locking screw which can be inserted in an internal thread in the cylindrical screw.

16. The articulation element as set forth in claim 11, wherein a hollow spring enveloping the locking device is used as an anti-rotation device or as an additional anti-rotation device.

17. A one-piece clamp for clamping rods of an external fracture fixation system comprising:
molded polymeric first and second jaw elements having an axial bore therethrough, said jaw elements connected on a first side of said axial bore by an integrally molded hinge element, each jaw element having a laterally open groove spaced from said axial bore on a second side thereof for receiving said rods, wherein the hinge includes two spaced resilient lateral bars, which each merge into the first and second jaw elements wherein the lateral bars each include a resilient and primarily C-shaped bar on the side of the clamp opposite the cavity, each of which merges into the first and second jaw elements wherein the lateral bars each have at least two complementary engagable part-cylindrically-shaped elements, one of which is a groove, acting as stops, which allow a pre-determined distortion about an axis of the resilient lateral bars before the stops come into engagement.

18. The clamp as set forth in claim 17, wherein the hinge includes a resilient hinge wall, which merges into two parallel ribs formed on said first and second jaw elements, which ribs run past the bore and which end in an area of a free end of at least one of the jaw elements or which merge into the body of the one jaw element.

19. The clamp as set forth in claim 18, wherein the lateral bars include a semi-circular centerpiece, followed at one end by a first bar portion having an end integral with a first side of the first jaw element and followed at a second end by a second bar portion integral with a first side of the second clamping jaw, the second bar portion longer than the first bar portion.

20. The clamp as set forth in claim 19, wherein the longer second bar portion is in the area of a wall adjacent to a cavity for receiving a rod and is connected with the second jaw element in the form of a rib.

* * * * *

UNITED STATES PATENT AND TRADEMARK OFFICE
CERTIFICATE OF CORRECTION

PATENT NO. : 7,241,074 B2 Page 1 of 1
APPLICATION NO. : 11/202690
DATED : July 10, 2007
INVENTOR(S) : Roland Thomke et al.

It is certified that error appears in the above-identified patent and that said Letters Patent is hereby corrected as shown below:

Column 1, line 7, "articulation, element" should read --articulation element,--.
Column 2, line 39, "being" should read --are--.
Column 2, line 43, "device is arranged" should read --device arranged--.
Column 2, line 61, "polymeric first" should read --polymeric with first--.
Column 7, line 45, "pressed in" should read --pressed-in--.
Column 7, line 46, "24 is a sign" should read --24 are a sign--.
Column 8, line 11, "hinge" should read --hinges--.
Column 8, line 13, "passes" should read --pass--.
Column 13, line 8, "portion longer" should read --portion being longer--.
Column 13, line 41, "jaw the first" should read --jaw of the first--.
Column 14, line 21, "elements" should read --element--.
Column 14, line 48, "portion longer" should read --portion being longer--.

Signed and Sealed this

Seventeenth Day of June, 2008

JON W. DUDAS
*Director of the United States Patent and Trademark Office*